US009038827B2

(12) United States Patent
Tseng

(10) Patent No.: US 9,038,827 B2
(45) Date of Patent: May 26, 2015

(54) PACKAGING BOX WITH TEST STRIPS AND GRIPPER ASSEMBLY THEREOF

(71) Applicant: Chao-Man Tseng, New Taipei (TW)

(72) Inventor: Chao-Man Tseng, New Taipei (TW)

(73) Assignee: K-JUMP HEALTH CO., LTD., New Taipei (TW)

( * ) Notice: Subject to any disclaimer, the term of this patent is extended or adjusted under 35 U.S.C. 154(b) by 207 days.

(21) Appl. No.: 13/666,754

(22) Filed: Nov. 1, 2012

(65) Prior Publication Data

US 2014/0116919 A1  May 1, 2014

(51) Int. Cl.
| | | |
|---|---|---|
| B65D 71/00 | (2006.01) | |
| G01N 33/487 | (2006.01) | |
| B65D 25/10 | (2006.01) | |
| B65D 71/70 | (2006.01) | |
| B01L 9/00 | (2006.01) | |

(52) U.S. Cl.
CPC .......... *G01N 33/4875* (2013.01); *B65D 25/107* (2013.01); *B65D 71/70* (2013.01); *B01L 9/527* (2013.01); *B01L 2200/025* (2013.01); *B01L 2300/0816* (2013.01); *B01L 2300/0825* (2013.01); *B01L 2300/0829* (2013.01)

(58) Field of Classification Search
CPC .. B65D 25/107; B65D 71/70; G01N 33/4875; A61B 5/1405; A61B 5/1433; A61B 5/14532; A61B 5/15142; A61B 5/15144; A61B 5/15151; B01L 9/527; B01L 2300/0829; B01L 2300/025; B01L 2300/0816; B01L 2300/0825
See application file for complete search history.

(56) References Cited

U.S. PATENT DOCUMENTS

| | | | |
|---|---|---|---|
| 5,690,233 A | 11/1997 | Kaneko | |
| 7,617,932 B2 * | 11/2009 | Windus-Smith et al. | ..... 206/363 |
| 2003/0223906 A1 | 12/2003 | McAllister et al. | |
| 2009/0098018 A1 | 4/2009 | Bainczyk et al. | |

FOREIGN PATENT DOCUMENTS

| | | |
|---|---|---|
| CN | 1216928 A | 5/1999 |
| CN | 1576184 A | 2/2005 |
| CN | 101124481 A | 2/2008 |
| DE | 10124944 C2 | 12/2002 |
| EP | 1118856 A1 | 7/2001 |

(Continued)

OTHER PUBLICATIONS

Office Action Dated Dec. 12, 2014 of the Corresponding Taiwan Patent Application No. 101116466.

(Continued)

*Primary Examiner* — Andrew Perreault
(74) *Attorney, Agent, or Firm* — Chun-Ming Shih; HDLS IPR Services

(57) ABSTRACT

A packaging box with test strips is provided for a gripper to grip the test strips, and the gripper has a gripping section and a conductive terminal in the gripping section, and the packaging box includes a main body and a test strip. The main body has an embedded groove including a port with a shape corresponding to the shape of the gripping section, and the port is provided for inserting the gripping section. The test strip has a conductive area defined on a surface of the test strip, and the test strip is contained in the embedded groove, wherein the gripping section is coupled to the port, and the conductive terminal is electrically coupled to the conductive area. With the packaging box, the test strips can be taken out conveniently and quickly.

3 Claims, 15 Drawing Sheets

(56) References Cited

FOREIGN PATENT DOCUMENTS

| | | |
|---|---|---|
| JP | 2004331171 A | 11/2004 |
| TW | 200533332 A | 10/2005 |

OTHER PUBLICATIONS

Office Action Dated Dec. 3, 2014 of the Corresponding China Patent Application No. 201210141268.8.

* cited by examiner

PACKAGING BOX WITH TEST STRIPS AND GRIPPER ASSEMBLY THEREOF

FIELD OF THE INVENTION

The present invention relates to a packaging box, in particular to the packaging box with test strips and a gripper assembly thereof.

BACKGROUND OF THE INVENTION

To meet the requirements of examination accuracy, test strips used in medical and scientific fields are generally packaged before use. The package can prevent the test strips from being moistened, damaged, or contacted with bacteria or contaminants in air, and the contaminated test strips may result in inaccurate test results.

In general, a conventional package for containing test strips comprises a bag and a test strip, and the bag has a containing space, and a port formed on a side of the containing space and provided for putting the test strip into the containing space and then sealing the port to package the test strip into the bag, so as to achieve the effects of isolating the test strip from contaminants or resisting moisture.

However, the conventional package for containing test strips still has the following drawbacks.

1. If it is necessary to take out the test strip, users have to tear open the package and grip an end of the test strip by fingers in order to remove the test strip from the bag, so that the test strip will be in contact with the users' fingers, and the bacteria and oil stains on the users' fingers may contaminate the test strip and affect the test results.

2. Since the test strip is taken out by fingers, the test strip must be manufactured specially with a fetching section for removing the test strip by fingers, and thus incurring additional material and manufacturing costs. Obviously, the conventional package for containing test strips requires improvements.

SUMMARY OF THE INVENTION

Therefore, it is a primary objective of the present invention to provide a packaging box with test strips, wherein the test strips are contained in the embedded groove to achieve the effect of removing the test strip from the packaging box easily.

To achieve the foregoing objective, the present invention provides a packaging box with test strips provided for a gripper to grip the test strips, and the gripper has a gripping section and a conductive terminal installed in the gripping section, and the packaging box comprises: a main body, having at least one embedded groove formed thereon, a port formed at the embedded groove and with a shape corresponding to the gripping section, and a notch extended from the port, and the port being provided for plugging the gripping section; and at least one test strip, having a conductive area defined on a surface of the test strip, and the test strip being contained in the notch, and the conductive area being exposed inside the port; wherein the gripping section is plugged into the port, and the conductive terminal is electrically coupled to the conductive area.

Another objective of the present invention is to provide a packaging box and a gripper assembly, wherein the test strips are contained in the embedded groove, and the gripper is passed into the embedded groove to clamp the test strip, so as to achieve the effect of removing the test strip by the gripper quickly.

To achieve the aforementioned objective, the present invention provides a packaging box and a gripper assembly comprising a gripper and a packaging box, wherein the gripper has a gripping section, and the gripping section has a conductive terminal installed therein; and the packaging box, comprises: a main body, having at least one embedded groove formed thereon, and the embedded groove include a port with a shape corresponding to the shape of the gripping section and a notch extended from the port, and the port being provided for plugging the gripping section; and at least one test strip, having a conductive area defined on a surface of the test strip, and the test strip being contained in the notch, and the conductive area being exposed inside the port; wherein the gripping section is plugged into the port, and the conductive terminal is electrically coupled to the conductive area.

The present invention further has the following effects. 1. The test strips are taken out by the gripper directly to avoid the users' fingers from touching the test strips or contaminating the test strip. 2. Since the test strip does not require any gripping section for their removal by fingers, the additional material and manufacturing costs of the test strip can be saved. 3. The gripping section has a shape corresponding to the shape of the port to prevent the gripper from being inserted into the main body from a wrong direction that causes the conductive terminal to be not in contact with the conductive area of the test strip and assure that when the gripper is inserted into the main body to grip the test strip each time, the conductive terminal can be electrically coupled to the conductive area. 4. The tearing structure is provided for piercing through the thin film, so that the gripper can be passed into the main body to grip the test strip more easily. 5. Since the frame is embedded and fixed with the positioning hole of the main body, the tearing structure can be prevented from moving freely on the main body.

DESCRIPTION OF THE PREFERRED EMBODIMENTS

The technical contents of the present invention will become apparent with the detailed description of preferred embodiments accompanied with the illustration of related drawings as follows.

Figure 1:
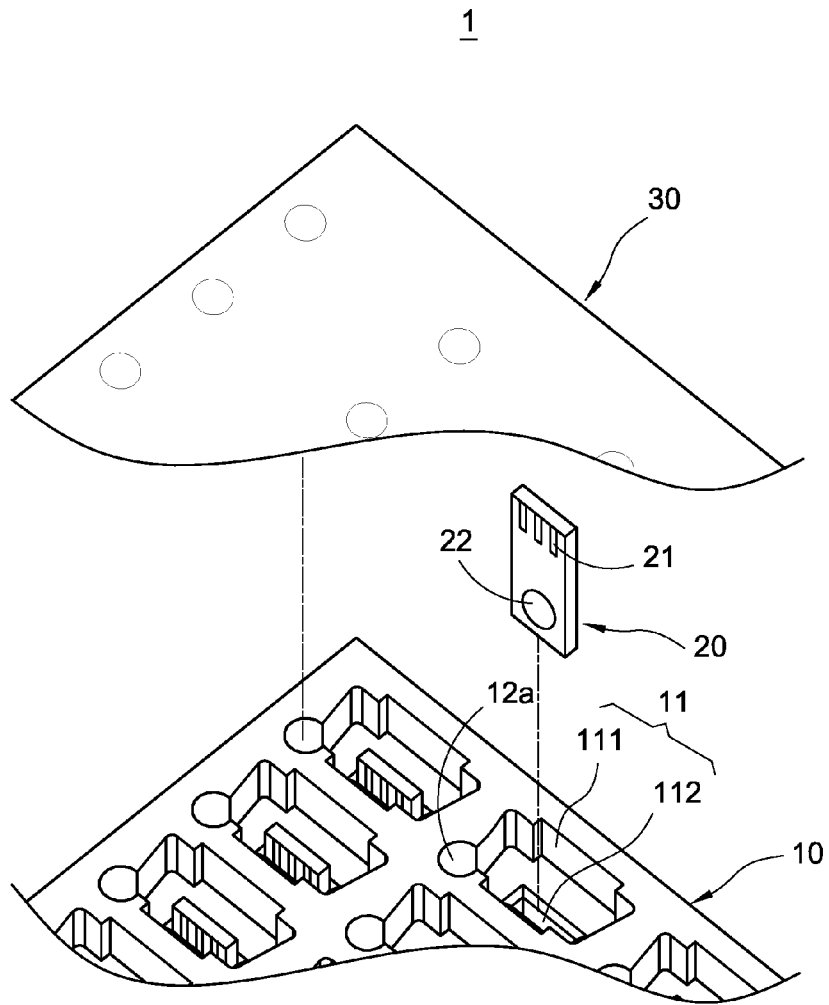
FIG. 1 is an exploded view of a first preferred embodiment of the present invention.
Figure 2:
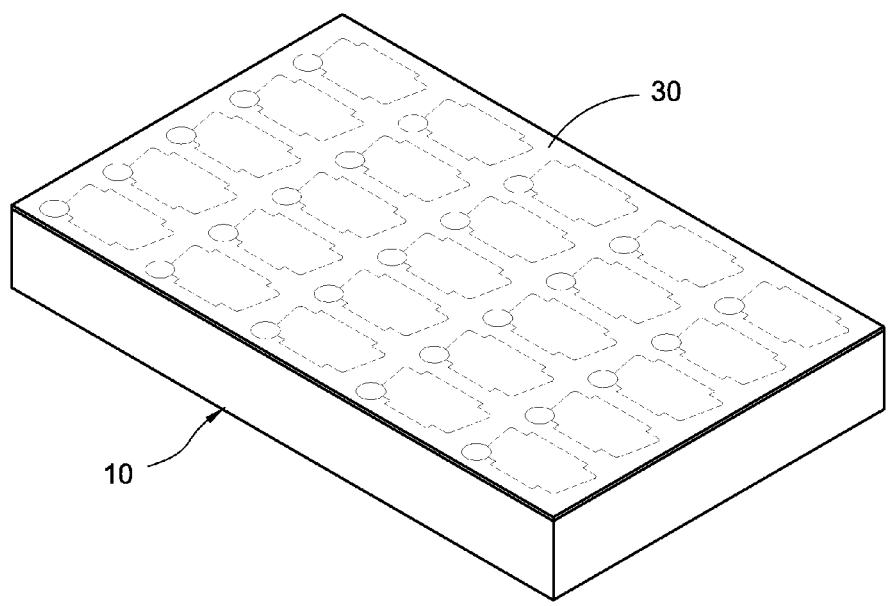
FIG. 2 is a perspective view of the first preferred embodiment of the present invention.
Figure 3:
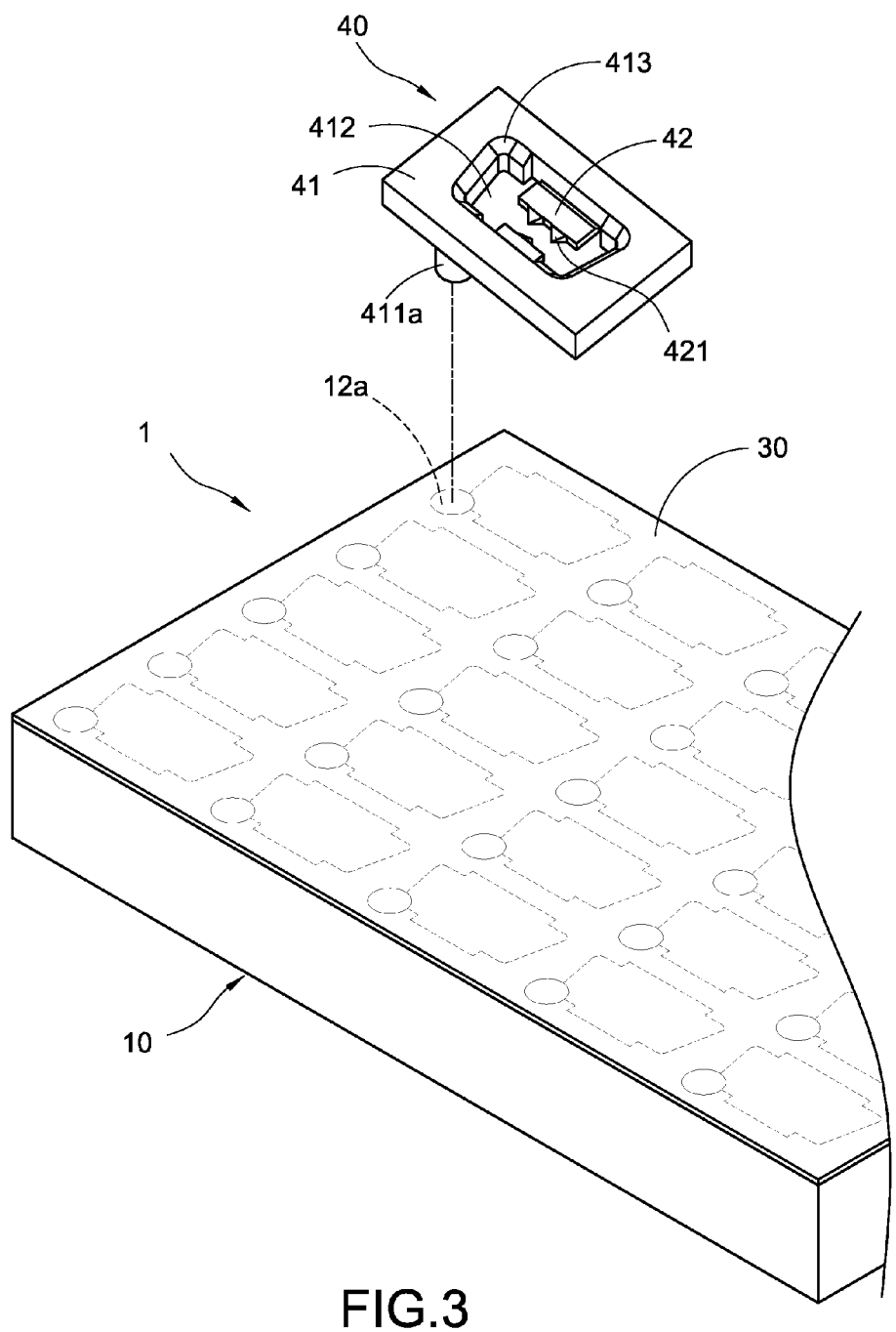
FIG. 3 is a schematic view of the first preferred embodiment of the present invention.
Figure 5:
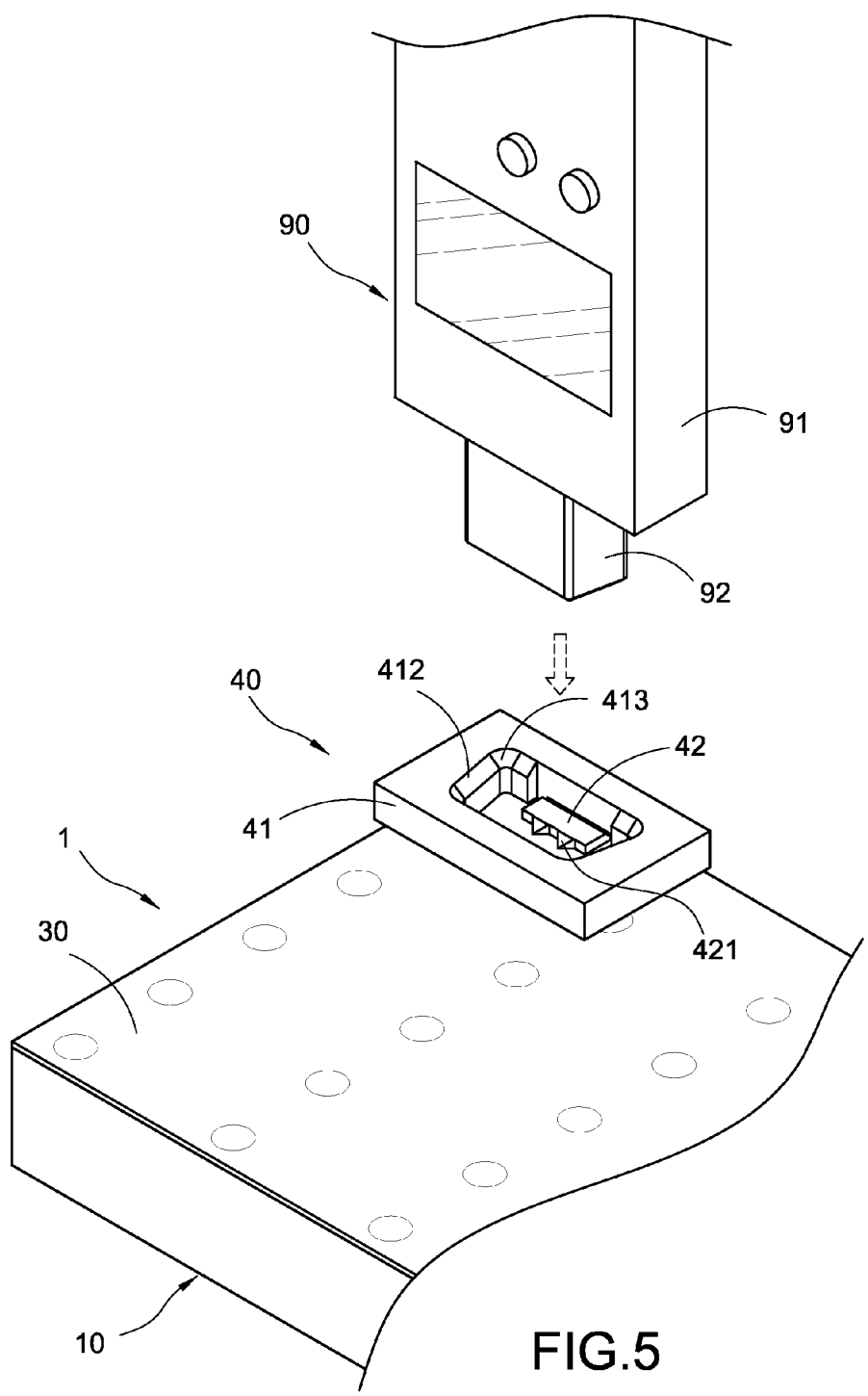
FIG. 5 is a first schematic view of a using status of the first preferred embodiment of the present invention.
Figure 6:
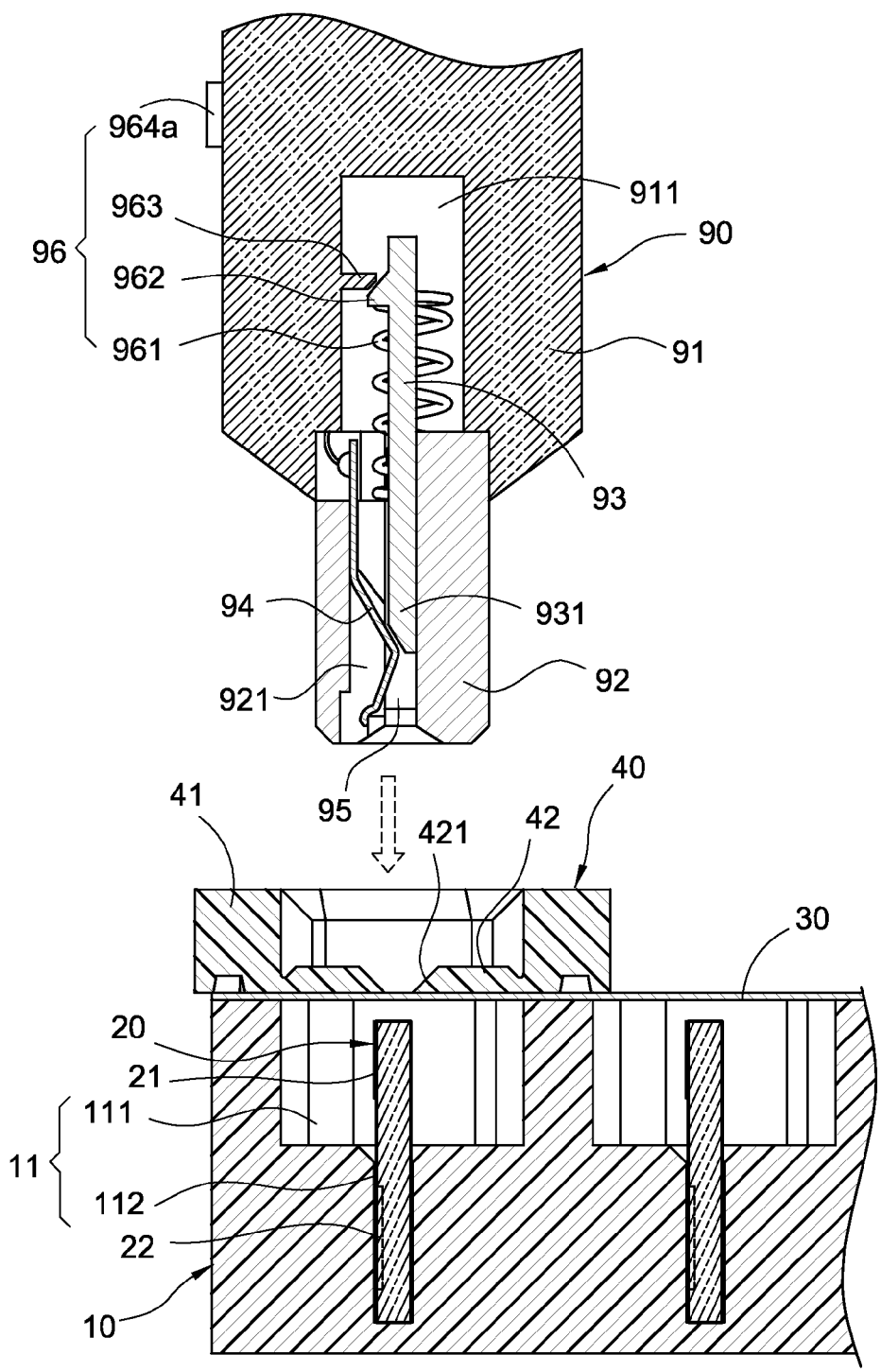
FIG. 6 is a second schematic view of a using status of the first preferred embodiment of the present invention.
Figure 7:
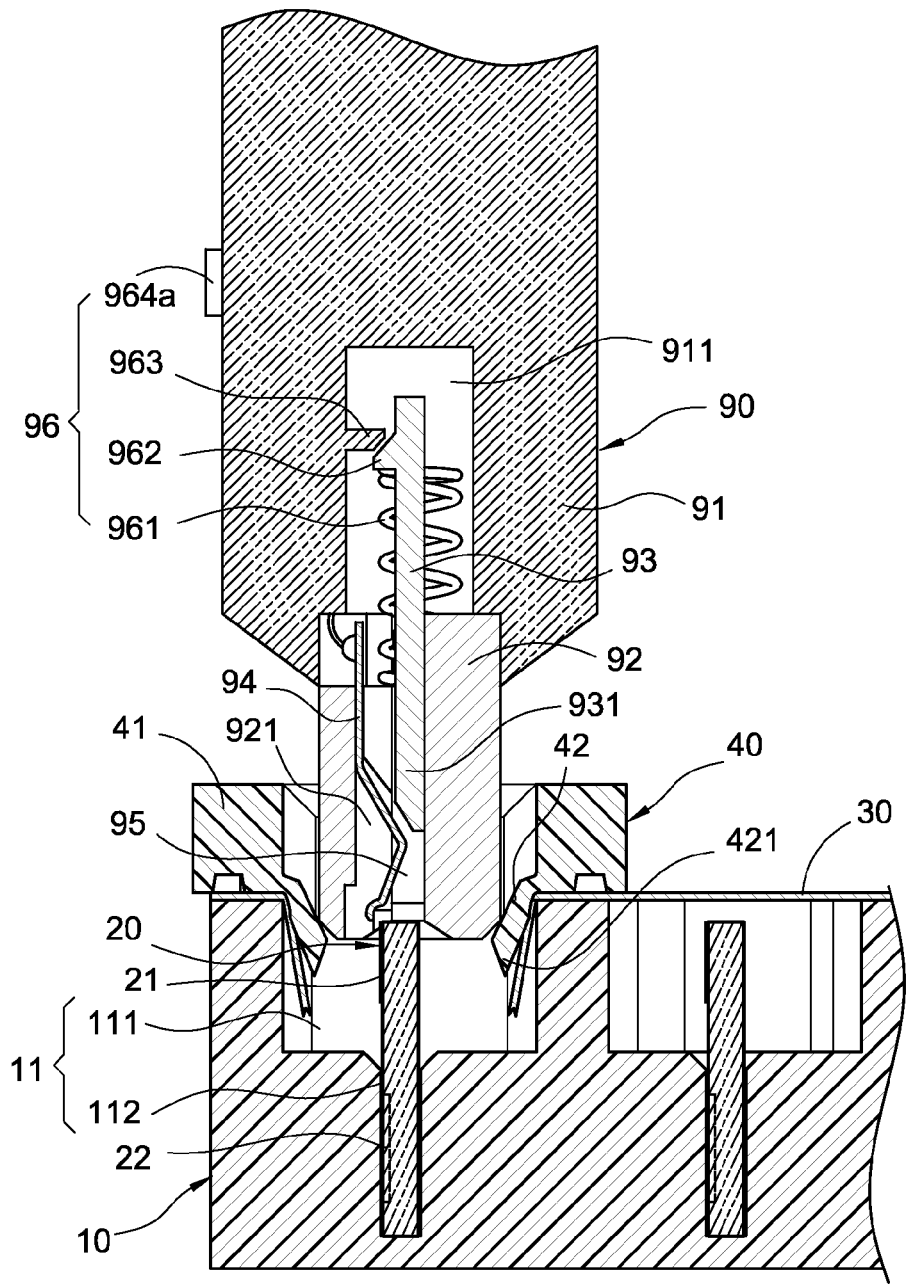
FIG. 7 is a third schematic view of a using status of the first preferred embodiment of the present invention.
Figure 8:
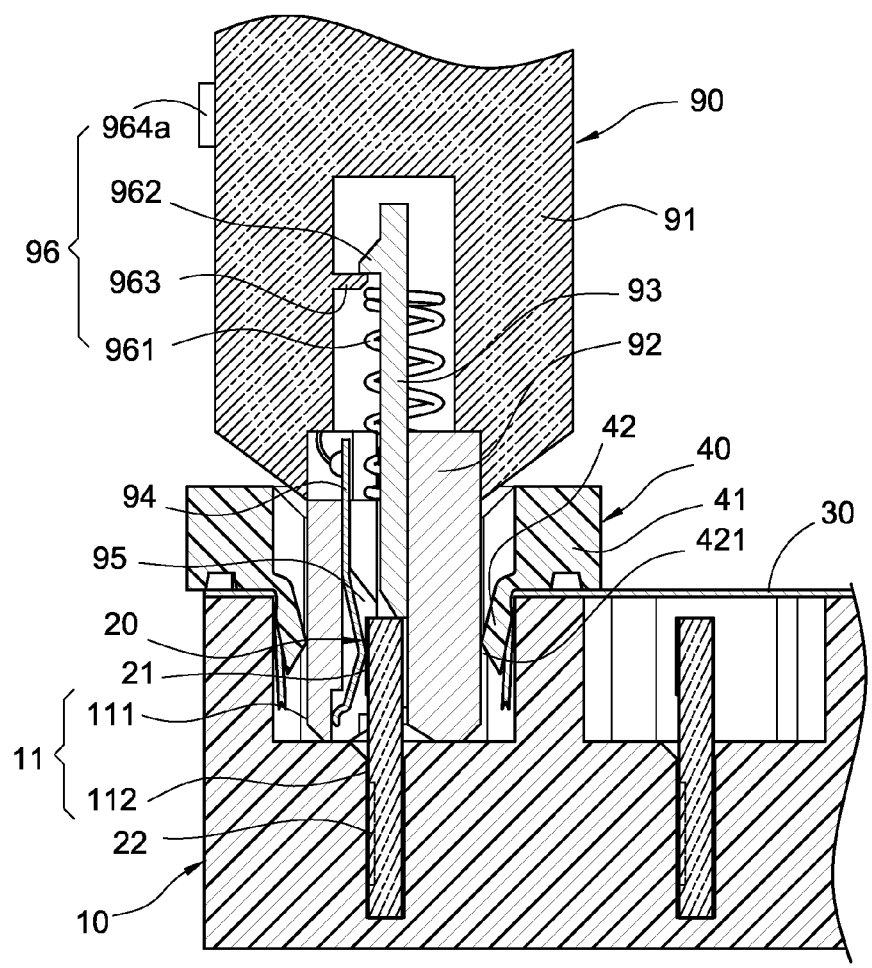
FIG. 8 is a fourth schematic view of a using status of the first preferred embodiment of the present invention.

With reference to FIGS. 1 to 3 for an exploded view, a perspective view and a schematic view of the first preferred embodiment of the present invention respectively, the present invention discloses a packaging box 1 and an assembly of a gripper 90 (as shown in FIG. 5), and the packaging box 1 comprises a main body 10 and a test strip 20.

The main body 10 has at least one embedded groove 11 formed thereon, and the embedded groove 11 includes a port 111 and a notch 112, wherein the notch 112 is extended out from the port 111, and the port 111 is interconnected with the notch 112, and the port 111 is substantially in a trapezium shape; the main body 11 has a concave hole 12a formed at a position adjacent to the port 111, and the concave hole 12a can be in a square or circular shape, but the invention is not limited to these shapes only.

The test strip 20 can be a water quality test strip or a biological parameter test strip, but the invention is not limited to these strips only. The test strip 20 has a conductive area 21 defined on a surface of the test strip 20 and a reaction area 22 defined on the other surface of the test strip 20. The side of the reaction area 22 of the test strip 20 is inserted and contained in the notch 112, and the side of the conductive area 21 of the test strip 20 is exposed inside the port 111.

The packaging box 1 further includes a thin film 30 and a tearing structure 40, and the thin film 30 is disposed corresponding to the port 111 and coated and sealed onto the main body 10 to package the test strip 20 into the main body 10, wherein the thin film 30 can be an aluminum foil.

The tearing structure 40 includes a frame 41 and at least one piercing element 42, and the frame 41 is corresponsive to the port 111 and put onto the thin film 30. The frame 41 has at least one protruding pillar 411a protruded from a side proximate to the thin film 30 and embedded into the concave hole 12a for fixing the tearing structure 40 onto the main body 10 to prevent the tearing structure 40 to move freely on the main body 10. The frame 41 has an opening 412 formed thereon, and the opening 412 has a shape corresponding to the shape of the port 111, and an edge of the opening 412 has a rounded corner 413. The piercing element 42 is coupled to a lower edge of an inner wall of the opening 412 and proximate to the thin film 30, and the piercing element 42 has at least one piercing member 421 extended in a direction towards the center of the opening 412, and the piercing member 421 has a sharp shape, such that when an action force is applied to the piercing element 42, the piercing element 42 will be bent towards the thin film 30, so that the piercing member 421 of the piercing element 42 will pierce through the thin film 30.

Figure 4:
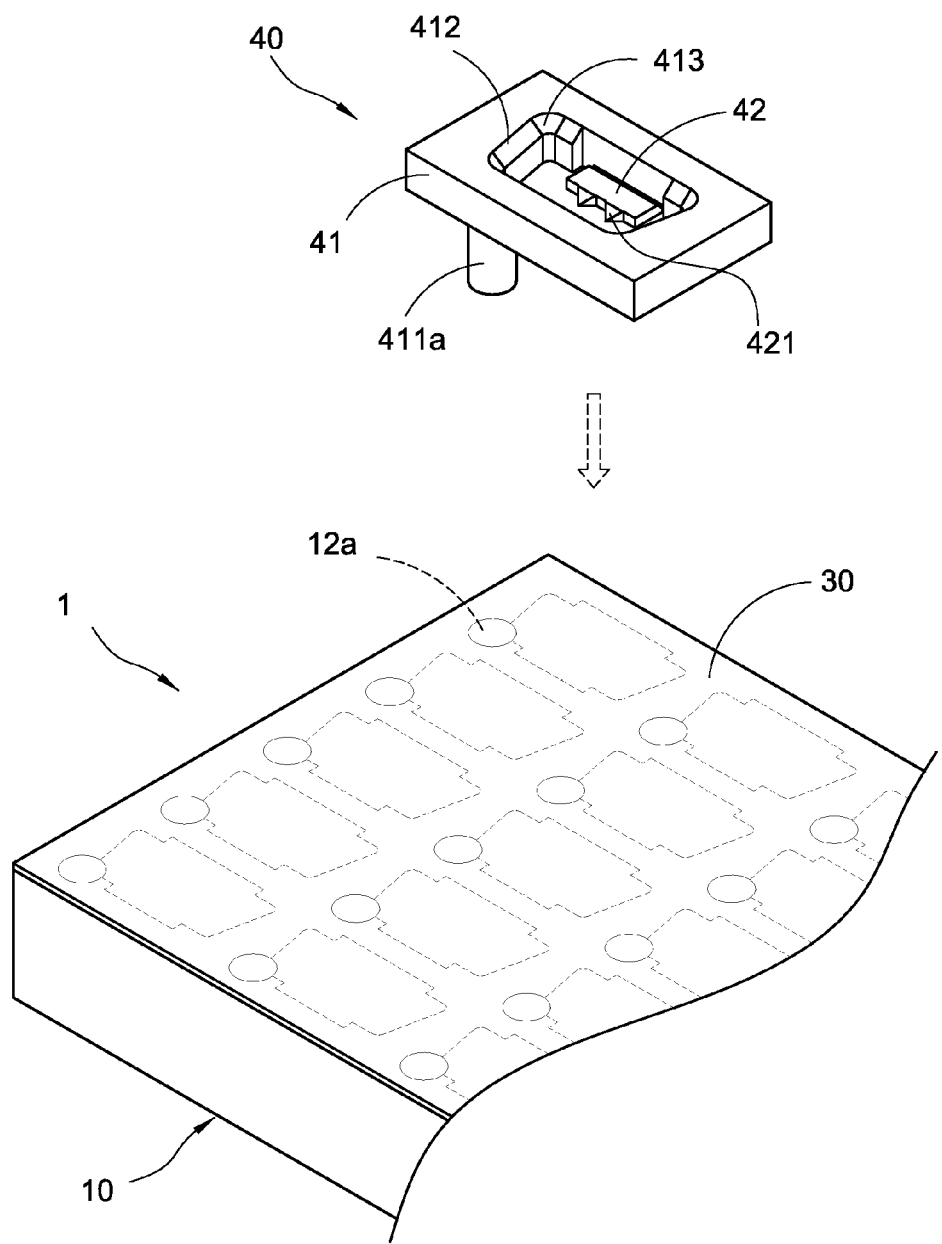
FIG. 4 is a schematic view of a using status of a tearing structure of the first preferred embodiment of the present invention.

With reference to FIG. 4 for a schematic view of a using status of a tearing structure in accordance with the first preferred embodiment of the present invention, the protruding pillar 411a of the frame 41 is aligned precisely and embedded into the concave hole 12a of the main body 10, and then the frame 41 is put onto main body 10 covered by the thin film 30, such that the effect of the protruding pillar 411a and the concave hole 12a embedded and fixed with one another can prevent the tearing structure 40 from moving freely on the main body 10.

With reference to FIGS. 5 to 8 for the first, second, third and fourth schematic views of using statuses of the first preferred embodiment of the present invention respectively, the gripper 90 includes a base 91, a gripping section 92, a tongue plate 93, a conductive terminal 94, a clamping space 95 and an eject mechanism 96, wherein an end of the gripping section 92 is coupled to an end of the base 91, and an end of the gripping section 92 away from the base 91 has a shape corresponding to the shape of the port 111. The gripping section 92 has a first accommodating chamber 921, and the base 91 has a second accommodating chamber 911, and the first accommodating chamber 921 is interconnected with the second accommodating chamber 911. A side of the tongue plate 93 is contained in the second accommodating chamber 911 and the other side of the tongue plate 93 has a clamping section 931 contained in the first accommodating chamber 921, and the conductive terminal 94 is installed in the first accommodating chamber 921 and corresponsive to the tongue plate 93. The clamping space 95 is defined between the conductive terminal 94 and the clamping section 931 for containing the test strip 20.

The eject mechanism 96 is installed between the tongue plate 93 and the base 91 and includes a spring 961, a first bump 962, a second bump 963 and a switch element 964a. The spring 961 is installed between the tongue plate 93 and the gripping section 92, and the first bump 962 is formed on a side surface of the tongue plate 93 disposed in the containing space 911, and the second bump 963 is disposed on an inner wall of the containing space 911 and the second bump 963 can be extended or retracted with respect to the inner wall of the containing space 911, and the second bump 963 and the first bump 962 are corresponsive to one another, and the second bump 963 can be latched with the first bump 962. The switch element 964a is installed on an external surface of the base 91 and linked with the second bump 963, and the switch element 964a can drive the second bump 963 to be extended or retracted.

If it is necessary to use the gripper 90 to grip the test strip 20, the gripping section 92 of the gripper 90 is passed into the opening 412 of the frame 41, so that an end of the gripping section 92 away from the base 91 presses against the piercing element 42 to bend in a direction towards the thin film 30, and the piercing member 421 of the piercing element 42 pierces through the thin film 30, and then the gripper 90 is pressed toward the embedded groove 11, and the gripping section 92 is passed into the embedded groove 11. Therefore, a side of the test strip 20 with the conductive area 21 is passed into the open slot 921 of the gripping section 92, and clamped into the clamping space 95 by the conductive terminal 94 and the tongue plate 93, and the conductive terminal 94 presses against the conductive area 21 of the test strip 20 to electrically couple the conductive terminal 94 with the conductive area 21. In the meantime, the tongue plate 93 is pushed slightly upward by the test strip 20, so that the first bump 962 disposed the on the tongue plate 93 is latched and fixed by the second bump 963. In addition, the gripper 90 can pierce through the thin film 30 directly without adopting the tearing structure 40 and is passed into the embedded groove 11 to grip the test strip 20.

Figure 9:
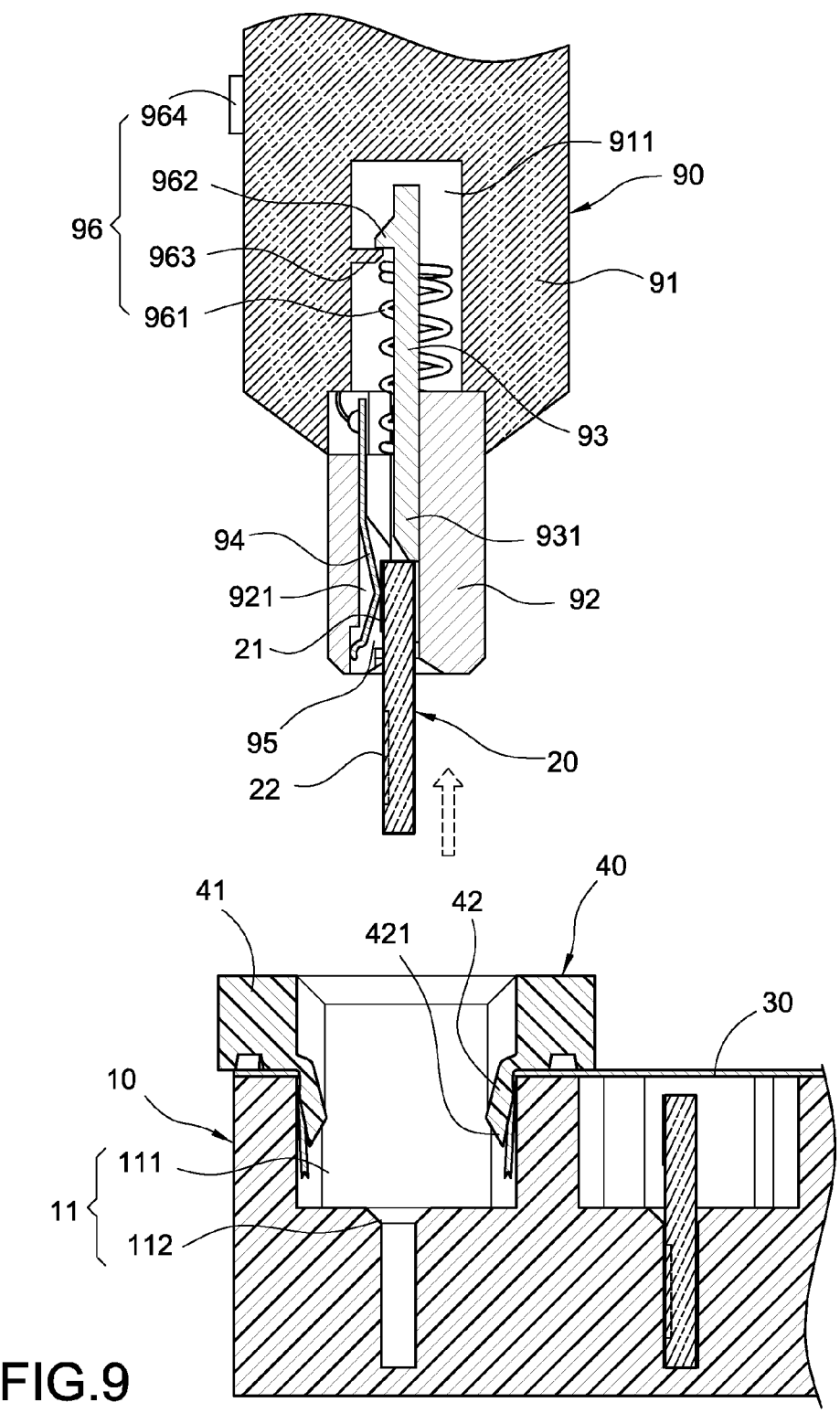
FIG. 9 is a fifth schematic view of a using status of the first preferred embodiment of the present invention.
Figure 10:
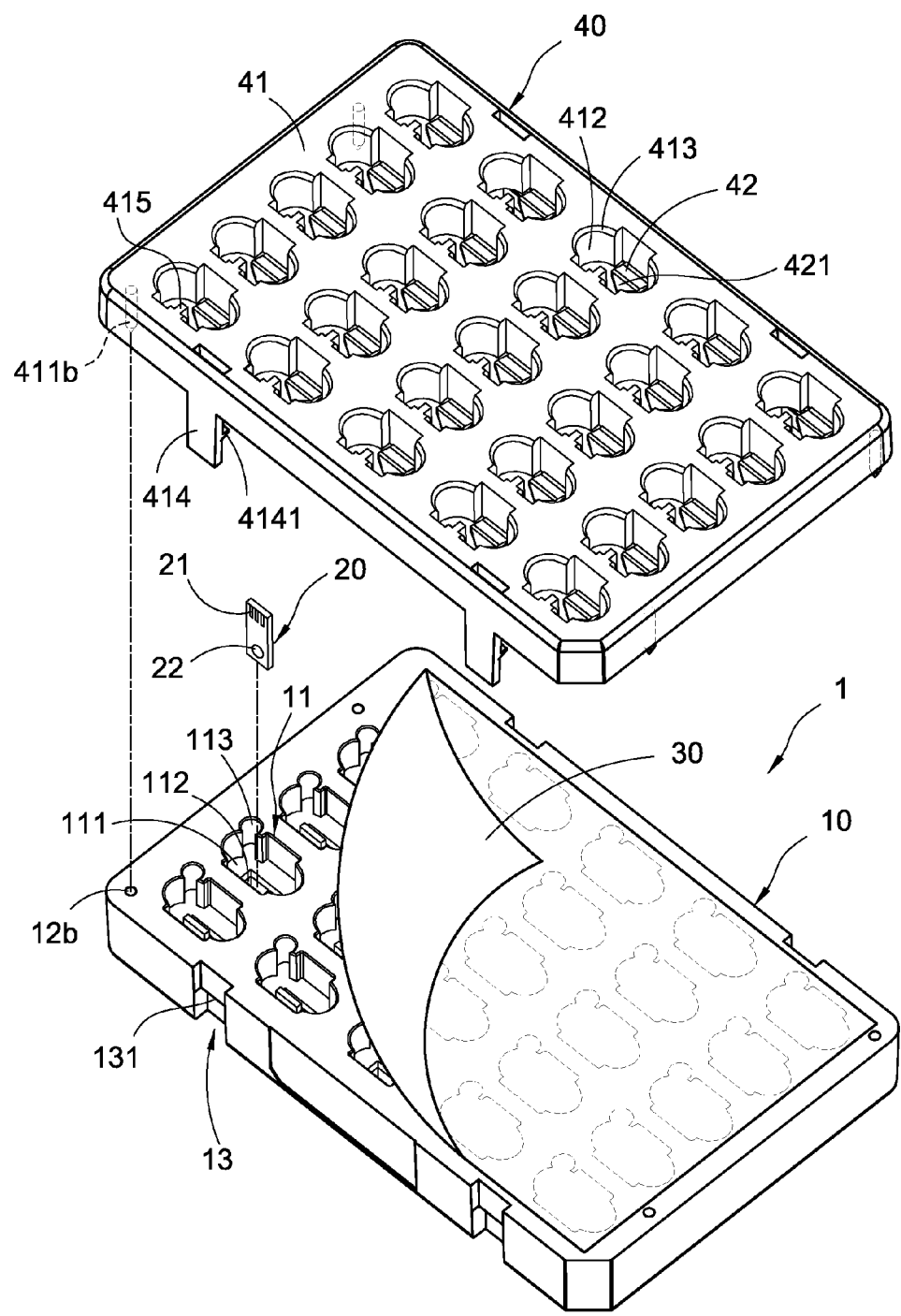
FIG. 10 is an exploded view of a second preferred embodiment of the present invention.
Figure 11:
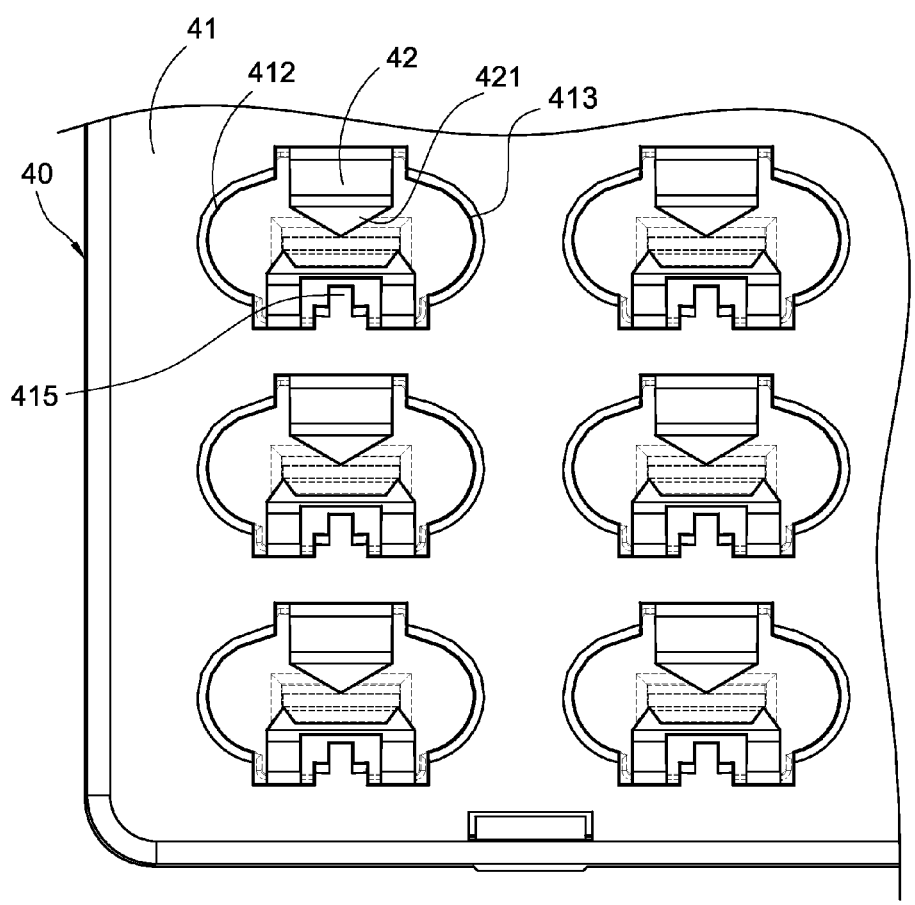
FIG. 11 is a schematic view of a using status of a tearing structure of the second preferred embodiment of the present invention.
Figure 12:
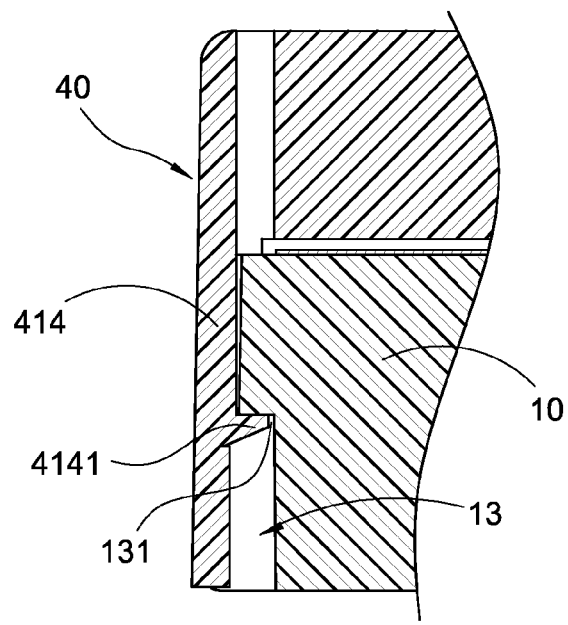
FIG. 12 is a first partial cross-sectional view of the second preferred embodiment of the present invention.
Figure 13:
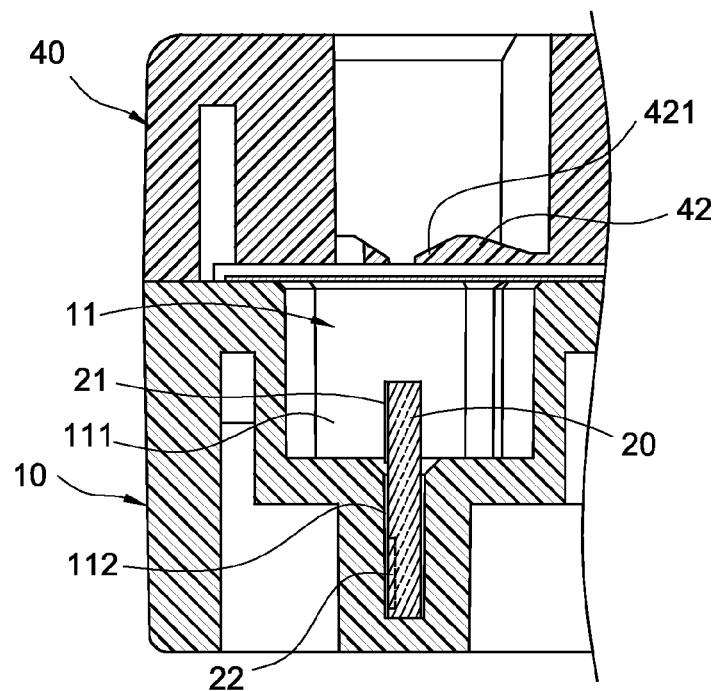
FIG. 13 is a second partial cross-sectional view of the second preferred embodiment of the present invention.

With reference to FIG. 9 for a fifth schematic view of a using status of the first preferred embodiment of the present invention, after the gripper 90 grips the test strip 20 in the packaging box 1, the gripper 90 is withdrawn from the packaging box 1 and away from the tearing structure 40.

In addition, the switch element 964a drives the second bump 963 to retract into the inner wall of the containing space 911. Now, the tongue plate 93 will be pulled back to its original position by the pulling force of the spring 961, so as to loosen the test strip 20 from the clamping space 95.

Wherein, the gripping section 92 has a shape corresponding to the shape of the port 111 to prevent the gripper 90 from being inserted into the main body 10 from a wrong direction which causes the conductive terminal 94 to be not in contact with the conductive area 21 of the test strip 20, so as to assure that when the gripper 90 is inserted into the main body 10 to grip the test strip 20 each time, the conductive terminal 94 can be electrically coupled to the conductive area 21. In addition, the test strip 20 is contained in the packaging box 1, and the gripper 90 can remove the test strip 20 directly to avoid touching the test strip 20 or contaminating the test strip 20. Further, the length of the test strip 20 can be smaller than that of the conventional test strip to save the material cost of the test strip 20.

With reference to FIGS. 10 to 13 for the exploded view of the second preferred embodiment of the present invention, the schematic view of a tearing structure, and the first and second partial cross-sectional views of the second preferred embodiment of the present invention respectively, the difference between the second preferred embodiment and the first preferred embodiment resides in that the concave hole 12a of the main body 10 is replaced by the concave hole 12b, and the protruding pillar 411a of the frame 41 is replaced by at least one protruding pillar 411b, wherein the concave hole 12b is formed at an edge of an end surface which is provided with the port 111 on the main body 11. At least one open slot 13 is formed on at least one side of the main body 10, and a latch slot 131 is formed on a wall of the open slot 13, and a through hole 113 is formed at the main body 10 and on a side of the port 111 and interconnected with the port 111 for placing an anti-blushing agent.

The protruding pillar 411b is formed and protruded from the frame 41 and proximate to an edge of an end surface of the thin film 30, and the protruding pillar 411b of the frame 41 is passed into the concave hole 12b of the main body 10, and at least one positioning pillar 414 is protruded from at least one side of the frame 41, and the positioning pillar 414 and the open slot 13 are embedded and fixed with one another. In addition, the positioning pillar 414 has a latch hook 4141 formed and protruded from a position proximate to a side of the open slot 13, and the positioning pillar 414 is latched with the latch slot 131 by the latch hook 4141 and embedded and fixed with the open slot 13. In addition, a bump 415 is protruded from an inner surface of the opening 412 of the frame 41, wherein the bump 415 is in an inverted T-shape, and a slide slot 922 (as shown in FIG. 14) is formed on a side of the gripping section 92 (as shown in FIG. 14) and corresponsive to the bump 415, and the bump 415 and the slide slot 922 (as shown in FIG. 14) are slidably coupled to each other to assure that when the gripper 90 (as shown in FIG. 14) is inserted into the main body 10 to grip the test strip 20, the conductive terminal 94 (as shown in FIG. 15) can be electrically coupled to the conductive area 21.

Figure 14:
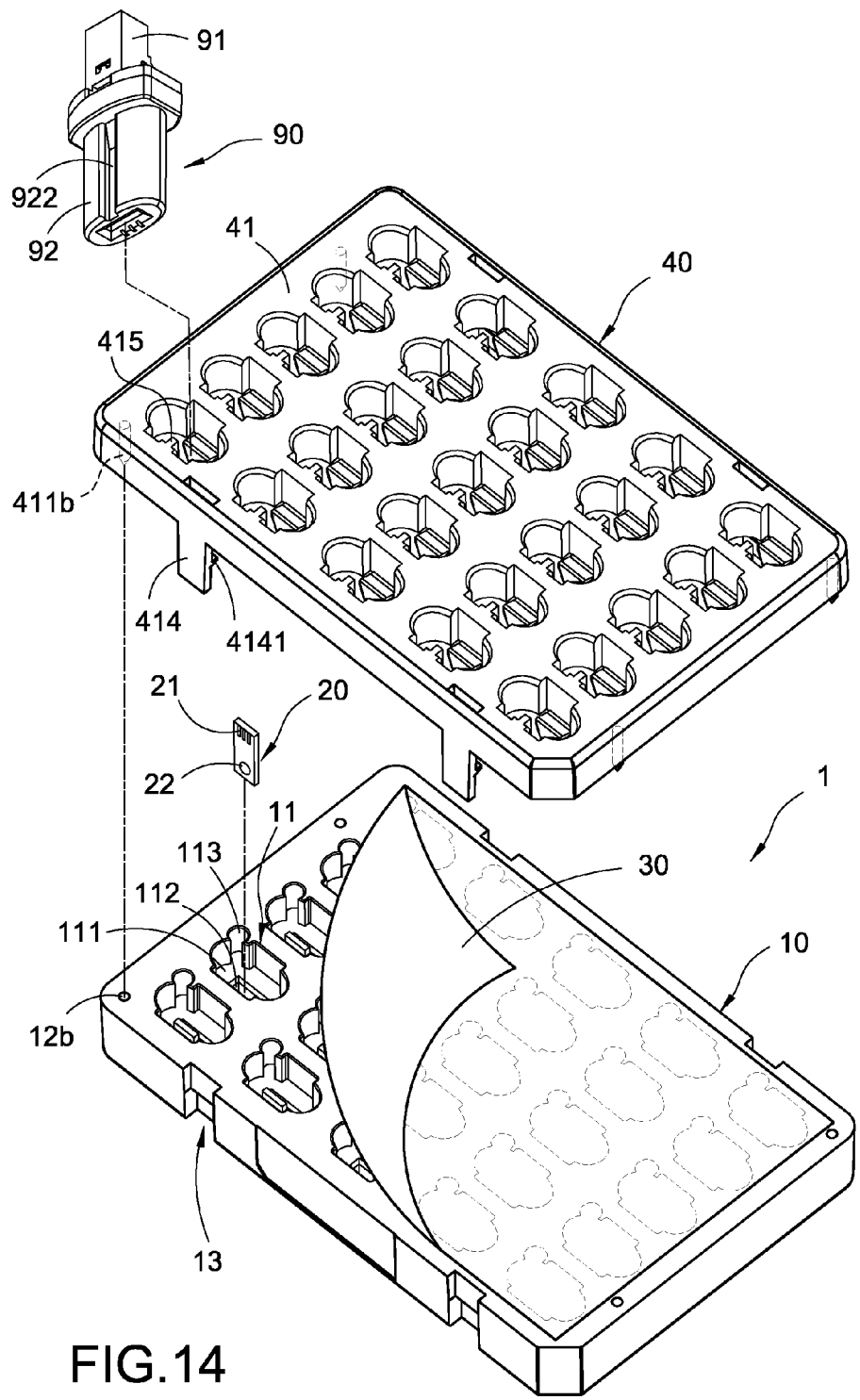
FIG. 14 is a perspective view of the second preferred embodiment of the present invention.
Figure 15:
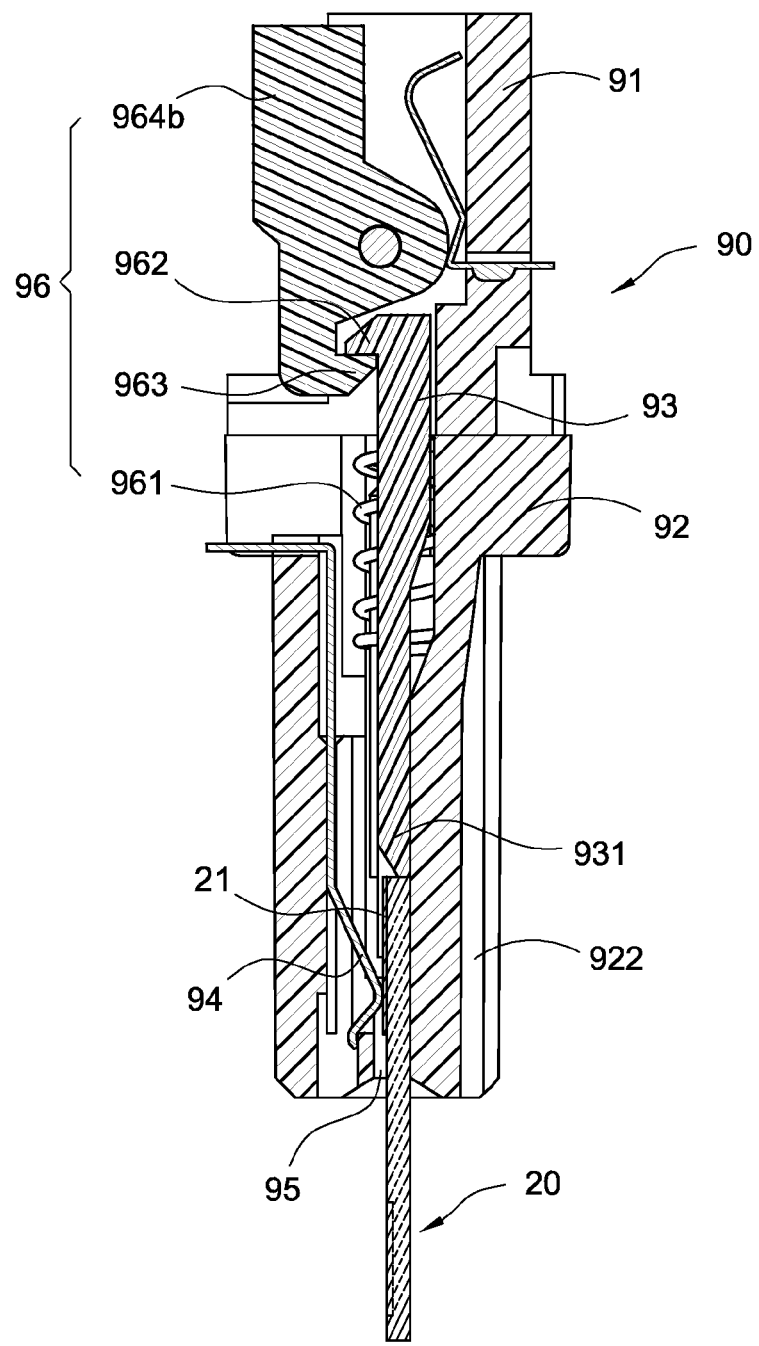
FIG. 15 is a first schematic view of a using status of a gripper of the second preferred embodiment of the present invention.
Figure 16:
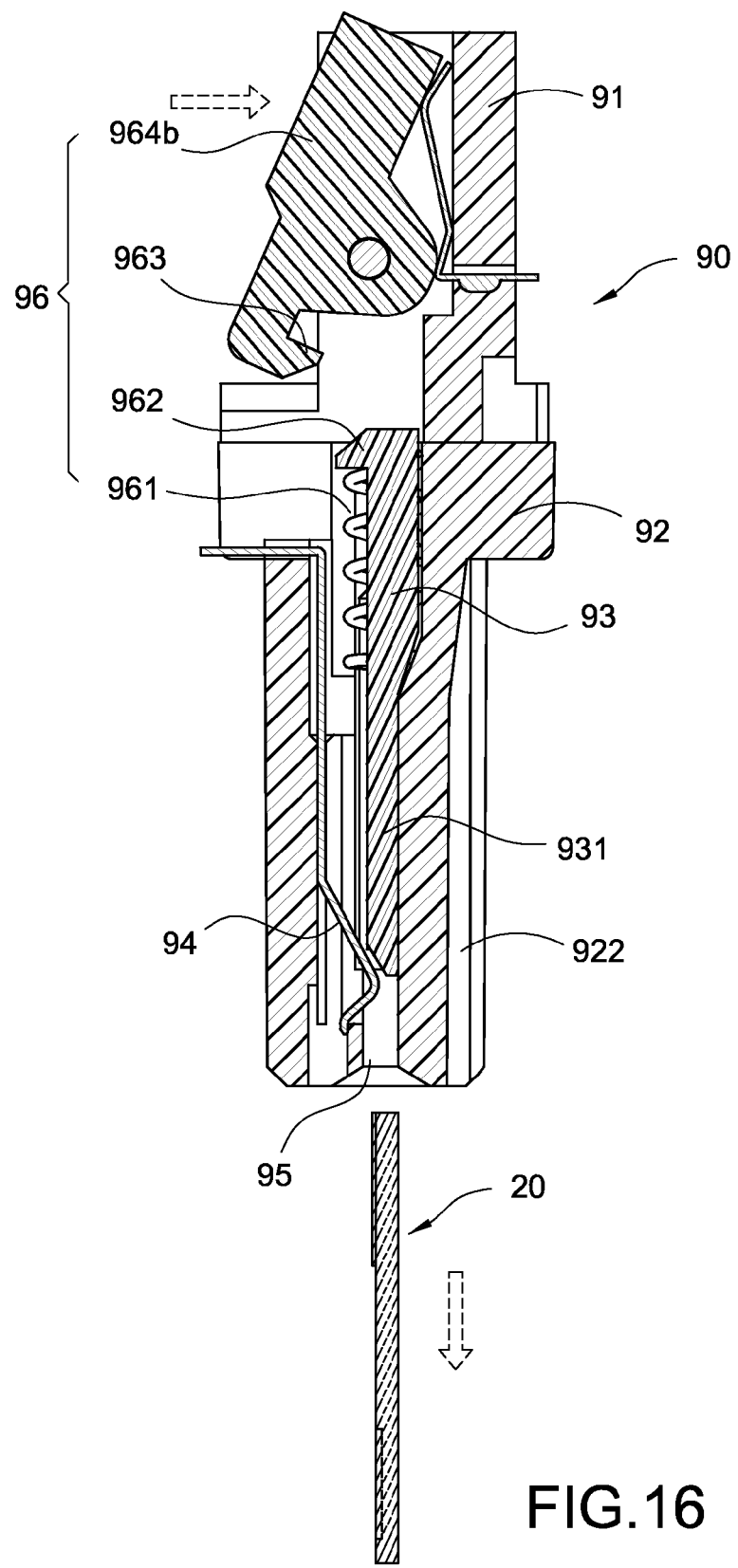
FIG. 16 is a second schematic view of a using status of a gripper of the second preferred embodiment of the present invention.

With reference to FIGS. 14 to 16 for a schematic view of the second preferred embodiment of the present invention, and the first and second schematic views of using statuses of the gripper in accordance with the second preferred embodiment of the present invention respectively, the switch element 964a is replaced by the latch plate 964b, and the latch plate 964b is pivotally coupled to the base 91, and the second bump 963 is formed and protruded from the latch plate 964b for moving the latch plate 964b, so that the first bump 962 can be latched to or loosened from the second bump 963.

If it is necessary to retract the gripper 90 from the test strip 20 after the gripper 90 grips the test strip 20, the latch plate 964b can be pressed to turn the second bump 963 away from the first bump 962 so as to loosen the second bump 963 from the first bump 962. Now, the tongue plate 93 will be pulled back to its original position by the pulling force of the spring 961, and the test strip 20 can be loosened from the clamping space 95 to withdraw the gripper 90.

In addition, the gripper 90 can pierce through the thin film 30 directly without any tearing structure 40 and can be passed into the embedded groove 11 to grip the test strip 20.

In summation of the description above, the present invention improves over the prior art and complies with the patent application requirements and thus is duly filed for patent application. While the invention has been described by means of specific embodiments, numerous modifications and variations could be made thereto by those skilled in the art without departing from the scope and spirit of the invention set forth in the claims.

What is claimed is:

1. A packaging box and gripper assembly, comprising:
   a gripper, having a gripping section, and the gripping section having a conductive terminal installed therein;
   a packaging box, comprising:
      a main body, having at least one embedded groove formed thereon, and the embedded groove include a port with a shape corresponding to a shape of the gripping section and a notch extended from the port, and the port being provided for plugging the gripping section; and
      at least one test strip, having a conductive area defined on a surface of the test strip, and the test strip being contained in the notch, and the conductive area being exposed inside the port;
   a thin film disposed corresponding to the port, and coated and sealed onto the main body; and
   a tearing structure, including at least one frame corresponding to the port and disposed on the thin film, and the frame having an opening formed thereon and a shape corresponding to a shape of the port,
   wherein, the gripping section is plugged into the port, and the conductive terminal is electrically coupled to the conductive area.

2. The packaging box and gripper assembly according to claim 1, wherein at least one protruding pillar is protruded from an end of the frame proximate to the thin film, and the main body has at least one concave hole formed at an end proximate to the thin film, and the protruding pillar is passed into the concave hole.

3. The packaging box and gripper assembly according to claim 1, wherein the tearing structure further comprises at least one piercing element coupled to an inner wall of the opening, and at least one piercing member formed and extended in a direction towards a center of the opening for piercing through the thin film.

* * * * *